United States Patent [19]

Rosenbaum et al.

[11] Patent Number: 4,837,006

[45] Date of Patent: Jun. 6, 1989

[54] PHOTOSTABLE COSMETIC COMPOSITION CONTAINING TRIHYDROXYETHYLRUTIN IN COMBINATION WITH WATER-SOLUBLE SUNSCREENS DERIVED FROM BENZYLIDENECAMPHOR AND ITS USE IN THE PROTECTION OF THE SKIN AND THE HAIR

[75] Inventors: Georges Rosenbaum, Asnieres; Jean F. Grollier, Paris, both of France

[73] Assignee: L'Oreal, Paris, France

[21] Appl. No.: 99,770

[22] Filed: Sep. 22, 1987

[30] Foreign Application Priority Data

Sep. 22, 1986 [LU] Luxembourg ............................ 86601

[51] Int. Cl.$^4$ .......................... A61K 7/06; A61K 7/42; A61K 7/44; A61K 9/12
[52] U.S. Cl. .......................................... 424/47; 8/405; 8/406; 424/DIG. 1; 424/59; 424/60; 424/61; 424/62; 424/63; 424/64; 424/70; 424/71; 424/72; 514/937; 514/944
[58] Field of Search ..................... 424/59, 60

[56] References Cited

U.S. PATENT DOCUMENTS

| | | | |
|---|---|---|---|
| 4,233,430 | 11/1980 | Jacquit et al. | 424/60 |
| 4,603,046 | 7/1986 | Georgalas et al. | 424/59 |

FOREIGN PATENT DOCUMENTS

| | | | |
|---|---|---|---|
| 1910561 | 9/1970 | Fed. Rep. of Germany | 424/70 |
| 677493 | 8/1952 | United Kingdom | 574/457 |

*Primary Examiner*—Dale R. Ore
*Attorney, Agent, or Firm*—Cushman, Darby & Cushman

[57] ABSTRACT

The invention relates to a photostable cosmetic composition for protection against UV rays with wavelengths between 280 and 400 nm, which contains, in a cosmetically acceptable aqueous or aqueous/alcoholic medium, trihydroxyethylrutin in combination with water-soluble sun-screens derived from benzylidenecamphor which are described in French Pat. Nos. 2,199,971, 2,236,515 and 2,282,426, and more particularly, 4-(2-oxo-3-bornylidenemethyl)phenyltrimethylammonium methylsulphate and 4-(2-oxo-3-bornylidenemethyl)benzenesulphonic acid and its metal or ammonium salts.

Application as a sunscreen composition for the skin, a protective composition for the hair or as a light-stabilized cosmetic composition.

11 Claims, No Drawings

PHOTOSTABLE COSMETIC COMPOSITION CONTAINING TRIHYDROXYETHYLRUTIN IN COMBINATION WITH WATER-SOLUBLE SUNSCREENS DERIVED FROM BENZYLIDENECAMPHOR AND ITS USE IN THE PROTECTION OF THE SKIN AND THE HAIR

The present invention relates to a photostable cosmetic composition for protection against ultraviolet rays, containing trihydroxyethylrutin in combination with water-soluble sunscreens derived from benzylidenecamphor and its use in the protection of the skin and the hair.

It is well known that the skin is sensitive to solar radiations which may cause a simple sunburn or erythema, but may also cause more or less serious burns.

However, solar radiations also have other harmful effects such as a loss of elasticity of the skin and the appearance of wrinkles leading to a premature ageing. Sometimes, even dermatoses may be observed. The extreme case is the occurrence of skin cancers in some subjects.

It is also desirable to ensure the provision to hair of a good protection against photochemical degradation in order to prevent a change in shade, a discoloration or a degradation of mechanical properties.

Moreover, it is known that constituents forming part of cosmetic preparations, and in particular some dyestuffs in dyeing compositions, colored lacquers for hair, shampoos, hair setting lotions, make-up products such as colored creams, nail varnishes and lipsticks, do not always have a sufficient light-stability and that they become degraded under the influence of light radiations.

It is well known that the most dangerous part of solar radiation consists of ultraviolet radiations with wavelengths less than 400 nm. It is also known that because of the presence of an ozone layer in the terrestrial atmosphere, which absorbs a part of the solar radiation, the lower limit of the ultraviolet radiation reaching the surface of the earth is in the region of 280 nm.

Consequently, it is desirable to have available compounds which are capable of absorbing ultraviolet radiations within the wavelength range from 280 to 400 nm, i.e. the UV-B rays with wavelengths between 280 and 320 nm, which play a preponderant role in causing solar erythema, as well as UV-A rays with wavelengths between 320 and 400 nm, which cause a browning of the skin and also the ageing thereof and which promote the onset of an erythematous reaction or enhance this reaction in some subjects or which may even be at the origin of phototoxic or photoallergic reactions.

The use of substances which filter ultraviolet radiations, in particular for protecting the skin against the harmful effects of sunlight, has already been recommended. Among these substances, some flavonoids and especially quercetin and rutin are known.

Flavonoids cover a wide range of structures which are classified into:
flavones and flavonols;
isoflavones, flavanones and dihydroflavonols;
chalcones and aurones; and
anthocyanidins and anthocyanins.

However, the production of compositions which are effective in protecting against UV radiations requires substances which filter within the wavelength range between 280 and 400 nm, which ensure a high degree of protection and which are at the same time sufficiently soluble in commonly used cosmetic media and which are stable against oxidation and against degradation due to atmospheric agents.

Now, none of the compounds belonging to the groups mentioned above has properties of ultraviolet radiation absorption within the range mentioned, sufficient solubility and photostability at the same time, which are required for them to be able to contribute to the preparation of compositions which give an adequately effective protection against ultraviolet radiations.

Water-soluble anthocyanidins and anthocyanins absorb outside the range of UV radiations reaching the earth's surface, viz. between 270 and 280 nm and within the visible range, viz. between 46 and 550 nm.

The remaining compounds mentioned above, for their part, indeed absorb within the range of the UV radiations concerned; however, they have the disadvantage of being practically insoluble in water, especially when these are polyhydroxylated compounds. These compounds are slightly more soluble in water when they are in the glucoside, diglucoside, rhamnoside, rhamnoglucoside or galactoside form and generally in the O-glucoside form. However, this increase in solubility still proves to be insufficient for these compounds to be able to contribute to the preparation of compositions effectively protecting against UV radiations within the range under consideration.

Now, the applicants have discovered, in a surprising way, that contrary to all expectations, trihydroxyethylrutin employed in combination with some known water-soluble sunscreens derived from benzylidenecamphor had a wide filtering power in the ultraviolet range within the wavelength range between 280 and 400 nm, a good watersolubility and a good stability against UV radiations at the same time and thus ensured a good protection against UV rays.

Therefore, the subject of the present invention is a photostable cosmetic composition which protects against ultraviolet rays with wavelengths between 280 and 400 nm, which contains, in a cosmetically acceptable aqueous or aqueous/alcoholic vehicle, an effective quantity of a combination of trihydroxyethylrutin and at least one other water-soluble sunscreen derived from benzylidenecamphor corresponding to the following formula:

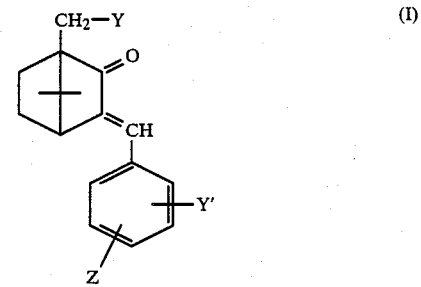

in which:
(i)
Y denotes a hydrogen atom,
Z is in the para position of the methylidene group and represents a group $-\overset{\oplus}{N}(CH_3)_2R$ in which R denotes a hydrogen atom or a $C_1$-$C_{12}$ alkyl radical, the ionic equilibrium of the molecule being achieved by an anion X<sup>⊖</sup> chosen from amongst halides, arylsulphonates, alkylsulphonates, camphosulphonates or alkylsulphates;

Y' denotes a hydrogen or halogen atom or a methyl radical;

these compounds are described in French Pat. No. 2,199,971;

(ii)

Y and Y' represent a hydrogen atom of an optionally salified $SO_3H$ radical, on condition that at least one of the two groups is other than a hydrogen atom, Y' being in the meta position of the methylidene group;

Z represents a halogen atom or $C_1$–$C_4$ alkyl radical;

these compounds are described in French Pat. No. 2,236,515; and (iii)

Y denotes a hydrogen atom or an optionally salified $SO_3H$ radical,

Z denotes an optionally salified $SO_3H$ and is in the para position of the methylidene group, and Y' denotes a hydrogen atom;

these compounds are described in French Pat. No. 2,282,426.

The sunscreens employed according to the invention have the important additional advantage of being well tolerated by the skin and of offering useful cosmetic properties.

Additionally, trihydroxyethylrutin which is a wideband filter, the absorption maximum of which is in the region of 348 nm, has antiinflammatory properties. Its use in a sunscreen composition for the skin is therefore particularly appropriate because it combines, with its effective filtering power, antiinflammatory properties which can be taken advantage of when erythemas caused by a prolonged exposure to solar radiations appear.

Another subject of the invention consists of a method for the protection of the skin and the hair, which may be natural or sensitized, against solar radiation, which consists in applying to the skin or to the hair an effective quantity of a photostable cosmetic composition as defined above.

"Sensitized hair" means hair which has undergone a permanent-waving, dyeing or bleaching treatment.

The invention also relates to a method for protecting a colored or uncolored cosmetic composition against solar radiation, which consists in incorporating into such a composition an effective quantity of trihydroxyethylrutin combined with a water-soluble derivative of benzylidenecamphor of the formula mentioned above.

The cosmetic composition according to the invention contains from 0.1 to 10% by weight of trihydroxyethylrutin and from 0.1 to 10% by weight of sunscreens derived from benzylidenecamphor of formula (I). The total concentration of sunscreens, trihydroxyethylrutin and sunscreens of formula (I), is between 0.2 and 20% by weight and preferably between 0.5 and 10% by weight relative to the total weight of the composition.

As UV-B ray filtering, water-soluble sunscreens derived from benzylidenecamphor combined with trihydroxyethylrutin according to the invention and described in French Pat. Nos. 2,199,971, 2,236,515 and 2,282,426 there may be mentioned, more particularly, 4-(2-oxo-3-bornylidenemethyl)phenyltrimethylammonium methylsulphate as well as 4-(2-oxo-3-bornylidenemethyl)benzenesulphonic acid, 2-methyl-5-(2-oxo-3-bornylidenemethyl)benzenesulphonic acid and 3-benzylidene-2-oxo-10-bornanesulphonic acid and their metal or ammonium salts.

Among the water-soluble UV-B filters above, the two preferred compounds are 4-(2-oxo-3-bornylidenemethyl)phenyltrimethylammonium methylsulphate and 4-(2-oxo-3-bornylidenemethyl)benzenesulphonic acid and its metal or ammonium salts.

The compounds according to the invention may also be combined with UV-A filters among which, there may be mentioned, in particular, benzene-1,4-[di(3-methylidene camphor)]-derivatives which are sulphonated on the methyl radical in position 10 of the camphor as described in French Pat. No. 2,528,420 and more particularly partially or totally neutralized benzene-1,4-[di(3-methylidenecamphosulphonic)]acid.

The total quantity of sunscreens employed in the cosmetic composition of the invention is between 0.5 and 20% by weight.

The sunscreens are solubilized in water or in an aqueous/alcoholic solution. The more particularly preferred monohydric or polyhydric alcohols contain 1 to 6 carbon atoms and are chosen from amongst ethanol, isopropanol, propylene glycol, glycerol and sorbitol; the aqueous/alcoholic solutions are preferably mixtures of water and ethanol.

The composition according to the invention may be in the various forms which are commonly employed for this type of composition. It may especially be present dissolved in the form of a lotion which is thickened to a variable degree, as an emulsion in the form of a cream or a milk, in the form of a pomade, or in the form of a gel or packaged as an aerosol.

When the cosmetic composition according to the invention is in the form of an emulsion forming a sunscreen composition, it is advantageous to dissolve a lipid-soluble sunscreen in the fatty phase, the trihydroxyethylrutin and benzylidenecamphor derivative of formula (I) being dissolved in the aqueous phase.

According to a first embodiment, the cosmetic composition according to the invention is intended to be applied onto the skin and contains cosmetic adjuvants commonly employed in this type of composition. As examples of these, there may be mentioned fats such as mineral, animal, vegetable or synthetic oils or waxes, fatty acids, fatty acid esters such as triglycerides of fatty acids containing 8 to 18 carbon atoms, fatty alcohols, emulsifiers and thickeners.

Among mineral oils, there may be mentioned liquid petrolatum; among animal oils, there may be mentioned whale, seal, menhaden, halibut liver, cod liver, tuna, turtle, suet, neat's-foot, horse's foot, sheep's foot, mink, otter and marmot oils; among vegetable oils, there may be mentioned almond, peanut, wheat germ, olive, corn, jojoba, sesame, sunflower, palm and walnut oils.

Among fatty acid esters, there may be mentioned isopropyl esters of myristic, palmitic and stearic acids and fatty esters which are solid at 25° C.

Fats such as vaseline, paraffin, lanolin, hydrogenated lanolin, acetylated lanolin and silicone fluids may also be employed.

Among waxes, there may be mentioned Sipol wax, lanolin wax, beeswax, Candelilla wax, microcrystalline wax, Carnauba wax, spermaceti, cocoa butter, karite nut butter, silicone waxes, hydrogenated oils which are solid at 25° C., and sugar glycerides, oleates, myristates, linoleates and stearates of Ca, Mg, Zn and Al.

Among fatty alcohols, there may be mentioned lauryl, cetyl, myristyl, stearyl, palmityl and oleyl alcohols.

Among emulsifiers, which may be nonionic, anionic, cationic or amphoteric, there may be mentioned polyoxyethylenated or polyglycerolated fatty alcohols such as, for example, lauryl, cetyl, stearyl and oleyl alcohols, containing from 2 to 30 moles of ethylene oxide.

Among thickeners, there may be mentioned cellulose derivatives, polyacrylic acid derivatives, and guar, carob and xanthan gums.

The cosmetic composition according to the invention may also contain other adjuvants commonly employed in cosmetics and especially moisturizers, softeners, coloring agents, opaqueing agents, preservatives and perfumes.

It may optionally contain a pH regulating agent. The pH is between 4 and 9, and preferably between 5.5 and 8.

In the case of a composition packaged as an aerosol, conventional propellants such as alkanes, fluoroalkanes and chlorofluoroalkanes are employed.

According to another embodiment, the cosmetic composition according to the invention is intended for protecting natural or sensitized hair against UV rays.

This composition may be in the form of a shampoo, a lotion, a gel or emulsion to be rinsed, to be applied before or after shampooing, before or after dyeing or bleaching, or before or after permanent-waving, a hairstyling or treatment lotion or gel, a blow-drying or hair setting lotion or gel, a hair lacquer, or a composition for permanent-waving, dyeing or bleaching the hair. In addition to the compound of the invention, this composition may contain various adjuvants commonly employed in this type of composition, such as surface-active agents, thickeners, polymers, softeners, preservatives, foam stabilizers, electrolytes, organic solvents, silicone derivatives, oils, waxes, antigrease agents, dyestuffs and/or pigments which have the role of coloring the composition itself or the hair, or any other ingredient commonly employed in the field of hair.

When the composition forms a shampoo, the latter is essentially characterized in that it contains at least one anionic, nonionic or amphoteric surface-active agent or their mixture and a compound according to the invention, in an aqueous medium.

When the composition forms an unrinsed lotion—blow-drying lotion, hair setting lotion, hair styling or treatment lotion—in addition to the compound according to the invention, it generally contains, in an aqueous or aqueous/alcoholic solution, at least one cationic, anionic, nonionic or amphoteric polymer or mixture thereof, in quantities of between 0.1 and 10%, and preferably between 0.1 and 3% by weight, and optionally antifoaming agents.

When the composition forms a lotion which is rinsed, which is also called a rinse, it is applied before or after dyeing or bleaching, before or after permanent-waving, before or after shampooing or between two stages of shampooing, and then rinsed after an exposure time.

This composition may be an aqueous or aqueous/alcoholic solution optionally containing surfactants, an emulsion or a gel. This composition may also be pressurized as an aerosol.

The invention also relates to a cosmetic composition, the UV ray sensitive constituents of which are protected against light radiations by the presence of trihydroxyethylrutin combined with a benzylidenecamphor derivative as defined above, in an effective quantity which is generally between 0.2 and 20% and preferably between 0.5 and 10% by weight.

This composition containing one or more compounds which are particularly sensitive to ultraviolet radiations may be a hair composition such as a hair lacquer, a colored or uncolored hair setting lotion, a shampoo, a dyeing shampoo, a hair dyeing composition, or alternatively a make-up product such as a nail varnish, a make-up foundation, a lipstick or a skin treatment cream and in a general way any cosmetic composition which may present light-stability problems during storage, because of its constituents.

The following examples illustrate the invention without, however, limiting it.

EXAMPLE 1

A sunscreen cream (O/W emulsion) with the following composition is prepared:

| | |
|---|---|
| Trihydroxyethylrutin | 1.00 g |
| 4-(2-oxo-3-bornylidenemethyl)benzenesulphonic acid | 4.00 g |
| Mixture containing 80% of cetylstearyl alcohol and 20% of oxyethylenated cetylstearyl alcohol containing 33 moles of ethylene oxide | 6.50 g |
| Non- self-emulsifiable glycerol monostearate and distearate mixture | 2.00 g |
| Cetyl alcohol | 1.70 g |
| Liquid petrolatum | 12.00 g |
| Propylene glycol | 2.50 g |
| Triethanolamine qs pH = 5 | |
| Preservative, perfume qs | |
| Water qs | 100.00 g |

EXAMPLE 2

A sunscreen milk (O/W emulsion) with the following composition is prepared:

| | |
|---|---|
| Trihydroxyethylrutin | 2.00 g |
| 4-(2-oxo-3-bornylidenemethyl)phenyltrimethylammonium methylsulphate prepared according to Example 1 of French Patent No. 2,199,971 | 4.00 g |
| Sodium lactate | 1.00 g |
| Cetyl alcohol | 1.00 g |
| Oxyethylenated oleocetyl alcohol containing 30 moles of ethylene oxide | 5.00 g |
| Stearyl alcohol | 4.00 g |
| Palmitic ester of 2-ethylhexyl glyceryl ether | 2.00 g |
| Purcellin oil (stearyl octanoate) | 2.00 g |
| Liquid petrolatum | 8.00 g |
| Propylene glycol | 4.00 g |
| Preservative, perfume qs | |
| Water qs | 100.00 g |

We claim:

1. Photostable cosmetic composition for protection against UV rays with wavelengths between 280 and 400 nm, which contains, in a cosmetically acceptable aqueous or aqueous/alcoholic medium, an effective quantity of a combination of trihydroxyethylrutin and at least one other water-soluble sunscreen derived from benzylidenecamphor corresponding to the following formula:

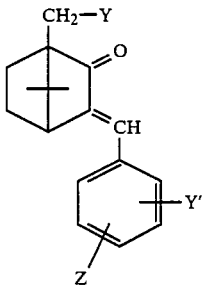 (I)

in which:

(i)
- Y denotes a hydrogen atom,
- Z is in the para position of the methylidene group and represents a group $-\overset{\oplus}{N}(CH_3)_2 R$ in which
- R denotes a hydrogen atom or a $C_1$–$C_{12}$ alkyl radical, the ionic equilibrium of the molecule being achieved by an anion $X^{\ominus}$ selected from halides, sulphonates, alkylsulphonates, camphosulphonates and alkylsulphates;
- Y' denotes a hydrogen or halogen atom or a methyl radical;

(ii)
- Y and Y' represent a hydrogen atom or an optionally salified $SO_3H$ radical, on condition that at least one of the two groups is other than a hydrogen atom, Y' being in the meta position of the methylidene group;
- Z represents a halogen atom or a $C_1$–$C_4$ alkyl radical;

(iii)
- Y denotes a hydrogen atom or an optionally salified $SO_3H$ radical,
- Z denotes an optionally salified $SO_3H$ and is in the para position of the methylidene group, and
- Y' denotes a hydrogen atom.

2. Cosmetic composition according to claim 1, wherein the remaining water-soluble agents which filter sunlight are UV-B filters derived from benzylidenecamphor, selected from 4-(2-oxo-3-bornylidenemethyl)-phenyltrimethylammonium methylsulphate, 4-(2-oxo-3-bornylidenemethyl)benzenesulphonic acid, 2-methyl-5-(2-oxo-3-bornylidenemethyl)benzenesulphonic acid and 3-benzylidene2-oxo-10-bornanesulphonic acid and the metal or ammonium salts of said acids.

3. Cosmetic composition according to claim 2, wherein the water-soluble UV-B filter derived from benzylidenecamphor is selected from 4-(2-oxo-3-bornylidenemethyl)phenyltrimethylammonium methylsulphate and 4-(2-oxo-3-bornylidenemethyl)benzenesulphonic acid and its metal or ammonium salts.

4. Cosmetic composition according to claim 1, which additionally contains UV-A
   filters selected from benzene-1,4-[di(3-methylidenecamphor)]derivatives which are sulphonated on the methyl radical in position 10 of the camphor.

5. Cosmetic composition according to claim 1, which contains from 0.1 to 10% by weight of trihydroxyethyl-rutin and from 0.1 to 10% by weight of water-soluble sunscreens derived from benzylidenecamphor of formula (I).

6. Cosmetic composition according to claim 1, intended to be applied onto the skin, which additionally contains at least one cosmetic adjuvant selected from lower monohydric alcohols or polyhydric alcohols containing 1 to 6 carbon atoms, mineral, animal, vegetable or synthetic oils or waxes, fatty acids, fatty acid esters, fatty alcohols, emulsifiers, thickeners, moisturizers, softeners, colouring agents, opaqueing agents, preservatives, perfumes, pH regulating agents and propellants.

7. Cosmetic composition according to claim 6, which is in the form of a lotion, an emulsion, a pomade, a gel of an aerosol.

8. Cosmetic composition according to claim 7, in the form of an emulsion, wherein the fatty phase contains a lipid-soluble sunscreen.

9. Cosmetic composition according to claim 1 which has a pH of between 4 and 9.

10. Cosmetic composition according to claim 1 which has a pH of between 5.5 and 8.

11. Method for protecting the skin and the hair against sunlight, which consists in applying to the skin or to the hair an effective quantity of a cosmetic composition according to claim 1.

* * * * *